_United States Patent_ [19]

Frank

[11] 4,417,585

[45] Nov. 29, 1983

[54] LIQUID MONITOR

[76] Inventor: Ulrich A. Frank, 945 Stuart Rd., Princeton, N.J. 08540

[21] Appl. No.: 288,658

[22] Filed: Jul. 30, 1981

[51] Int. Cl.$^3$ ............................ A61B 5/00; G01F 3/24
[52] U.S. Cl. .................................. 128/668; 128/771; 604/246; 73/219
[58] Field of Search ............... 128/771, 768, 762, 760; 73/219, 217, 218; 604/245, 246

[56] References Cited

U.S. PATENT DOCUMENTS

| 101,125 | 0/1870 | Hargrave | 73/219 X |
| 286,285 | 0/1883 | Erwin | 73/219 X |
| 3,630,081 | 12/1971 | Nelson | 73/219 |
| 3,943,762 | 3/1976 | Baer | 73/219 X |
| 4,030,356 | 6/1977 | Jaquith | 73/219 X |
| 4,130,273 | 12/1978 | Woog | 73/219 X |

FOREIGN PATENT DOCUMENTS

| 2416875 | 10/1974 | Fed. Rep. of Germany | 73/219 |
| 2377613 | 9/1978 | France | 73/219 |
| 1590374 | 6/1981 | United Kingdom | 73/219 |

_Primary Examiner_—Edward M. Coven
_Assistant Examiner_—John C. Hanley
_Attorney, Agent, or Firm_—Weinstein & Sutton

[57] ABSTRACT

A device to digitally meter, monitor and collect liquid, such as urine, from a catheterized patient. As such it is the successor to and improvement upon U.S. Pat. No. 3,769,497. An optional part prevents the migration of bacteria from the monitoring and collecting devices to the patient's body cavity. The device comprises a plurality of uniquely shaped movable containers that empty their contents when filled to a predetermined volume, a catheter for delivering liquid to the containers, movement sensors for detecting container movement to determine the amount of fluid collected, patient isolating means for electrically isolating the sensors from the patient while delivering movement signals to the sensors, a final collection container for receiving liquid from the movable containers, supports for supporting the device, and controls and alarms for indicating an alarm condition.

8 Claims, 6 Drawing Figures

LIQUID MONITOR

BACKGROUND OF THE INVENTION

Reference U.S. Pat. No. 3,769,497, by the same inventor, was found to suffer from certain deficiencies that prevented its use. The present invention overcomes these deficiencies in addition to introducing some new concepts. While the concepts and configurations discussed here may be used in other applications for liquid measurements, their application to urine measurement will be stressed here.

Urine production of patients is one of the vital signs customarily monitored in hospitals. Its value is not limited merely to indications of renal functions, but it is also quite useful to gain insight into liquid balance, perfusion, cardiac output, edema, etc. Clinically, it is important to know the exact volume of urine discharged and the continuum of urine production. The cessation of urine production may be a warning of loss of proper contact between the patient and the catheter, clogging with kidney stones or other obstructions, or kinking of the catheter, or the degradation or even failure of physiological functions.

Several ways now exist to achieve one or all of these monitoring functions. In all of these, as indeed with the subject invention, the patient is catheterized by the insertion of the first end of a flexible plastic tube in the urethra. The opposite end of the tube communicates with the measuring means. The measuring means most commonly used is a transparent plastic bag, where the meniscus within the bag is evaluated against graduations arranged along the bag to determine the amount of liquid collected. Reading of the bag requires frequent observation by medical personnel to assure a continuum of urine production. Also, it is difficult to determine the recent addition of urine to a partially filled bag. Typically, this might require the determination of small additions to large existing volumes. Also, these bags do not have alarm provisions. One cause for such an alarm would be the unexpected appearance of gross hematuria.

Another means for measuring such fluid is by weighing the collected discharge. This technique permits the use of alarms if the rate of discharge deviates beyond previously set limits. This approach suffers from the high cost of circuit components, which normally include a strain gage load cell and highly stable voltage supplies.

Although various electrical means of liquid level determination have been proposed, they have been rejected due to their failure to provide adequate patient safety. It is considered poor practice to electrocute a patient through the electrically conductive urine.

SUMMARY OF THE INVENTION

The purpose of the present invention is to provide a safe, digitizing means to measure the urine flow rate and volume. This was also the objective of reference patent U.S. Pat. No. 3,769,497. However, the reference patent discloses a single tiltable container as the primary measuring means. A measuring cycle is typically comprised of a filling period and a dumping period. Unfortunately, an unknown and unmeasurable amount of liquid can be passed to the container during the dumping cycle. This source of inaccuracy is substantially overcome with reference to FIG. 2 of the present invention, which shows a bistable condition of either of two containers underneath a liquid entrance spout. Either one or the other of these containers is always under the spout and in the filling position. More than two containers could be utilized, if desired.

A second and more subtle source of potential measurement inaccuracy derives from the fact that urine varies in density. Therefore, any system based on weight or leverage would vary in direct proportion with density when measuring volume. This difficulty is overcome in the present invention by the unique shape of the container. Referring to FIG. 2, it is apparent that each container is made up of two differently shaped liquid receiving portions. The initial flow is collected in a first triangular-shaped collecting portion that is arranged symmetrically directly over the pivot point about which the container is swingably moved. This first collecting portion is by far the major volume and cannot contribute to the subsequent tilting torque due to its symmetrical arrangement about the pivot. Variation in density of the liquid therefore cannot contribute to variations in measured volume. The upper limit of the first liquid receiving portion is designated by wavy line 25 of FIG. 2. Filling beyond level 25 rapidly increases the torque experienced by the swingable container, which finally results in tilting the bistable device into its other stable position.

A third difficulty that may be overcome by the apparatus disclosed herein is the catheter induced infections that many catheterized patients suffer from. The nature of this invention is described in a paper by Weyrauch and Basset entitled "Ascending Infection in an Artificial Urinary Tract", published February 1951 in Vol. 9, No. 1 of the Stanford Medical Bulletin. In this reference we learn that the bacteria, typically escherichia coli and proteus vulgaris, will travel upstream through the urine from the collecting bag into the body cavity. This will occur even when the flow of urine is continuous in the opposite direction. It does not occur in the absence of urine.

The latter phenomena, that ascent does not occur in the absence of urine, gives us the clue to denying the bacteria its upstream mobility. Prior apparatus makes use of an airbreak to accomplish this. Yet, as splashing and shaking wets the walls of the airbreak chamber, a continuous path is unfortunately reestablished.

Assume, however, that a significant portion of the catheter, or its entire length, is extruded of a hydrophobic material such as tetrafluoroethylene. A characteristic of such hydrophobic material is that it cannot be wetted. U.S. Pat. No. 3,326,230 by the inventor makes use of this property of hydrophobic material whereby the wall of the catheter cannot remain wetted and coated with urine after the bolus of urine has passed. Thus, the path's continuity is impossible and infection is prevented. The entire catheter tube may be formed of the hydrophobic material or alternatively, the interior surface of the tube or tube section may be coated or otherwise treated with the hydrophobic material.

A condition that should cause an alarm is the unexpected appearance of blood in the urine. This gross hematuria condition can be ascertained by the altered ratio of two color-filtered fiberoptic bundles. FIG. 3 shows two fiberoptic bundles introducing light near the source aperture and thereby through the urine as it enters the metering chamber. Air and blood-free urine will establish a normal ratio of red and green filtered light. This ratio is upset when green absorption occurs due to the presence of red platelets. The control circuitry would make this alarm feature optional.

BRIEF DESCRIPTION OF THE FIGURES

A typical embodiment of the device is described in the drawings.

DETAILED DESCRIPTION OF THE INVENTION

Figure 1:
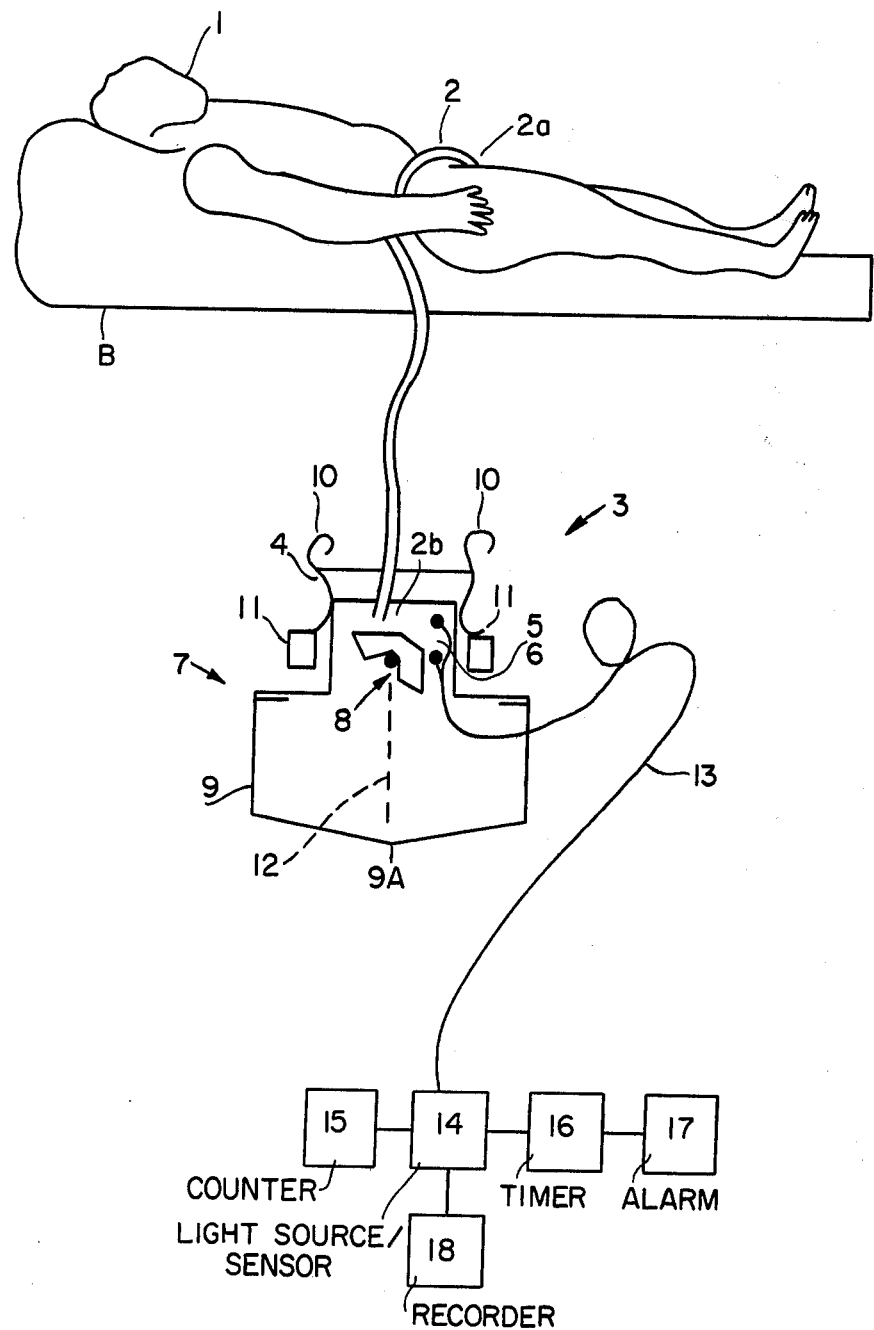
FIG. 1 shows the overall monitoring and alarm system.

FIG. 1 shows a patient 1 lying in a bed B. Patient 1 has the first end 2a of catheter 2 placed so as to communicate said first end 2a with the urinary bladder (not shown). The opposite end 2b of the catheter communicates with device 3. Device 3 is comprised of a reusable holder 4 with fiberoptic source and sensor 5 and mirror 6. Nested within the holder 4 is a disposable unit 7, whose principal components are a bistable tiltable mounted, opaque dual bucket assembly 8 and a collecting bag 9. Catheter 2 may have a portion of its interior or all of its interior coated with a hydrophobic material. Alternatively, catheter 2 may be totally formed of a hydrophobic material or have one section thereof formed of hydrophobic material. The section may be at either end of catheter 2 or may be intermediate the ends.

The device 3 is held by hooks 10 which are typically mounted upon the bedstead (not shown) for bed B or upon a freestanding stand. Numeral 11 designates a weight forming a part of the holding structure that keeps the device level prior to the accumulation of urine in the collecting bag. The weight 11 may be annular in shape and surround the device 3 or may be discrete weights symmetrically arranged about the periphery of device 3. The pivot 22 of the bistable buckets 8a and 8b (see also FIGS. 2a and 2b), the bottom-most point 9A of the collection bag 9, the suspension hooks (or hook) 10 and the weight or weights 11 are all symmetrically disposed around the center of gravity represented by imaginary vertical line 12.

Figure 3:
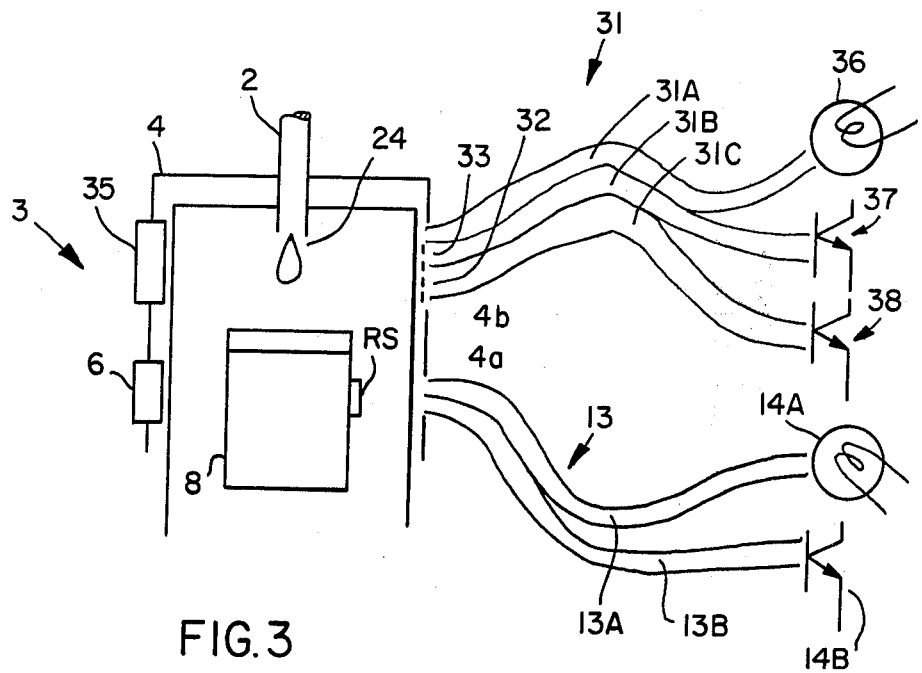
FIG. 3 is a side view of a portion of the metering device illustrating the light passage.

A dual fiberoptic bundle 13, shown in detail in FIG. 3, is comprised of a first light directing bundle 13A for directing light from a light source 14A, provided in circuit 14, towards mirror 6. The terminus of the dual fiberoptic bundle 13 is also held by reusable holder 4 at 4a to direct a light beam across the metering chamber. As further illustrated in FIG. 3, on the far side of the metering chamber is a mirror 6, also part of holder 4. The path of the light from the source fiber bundle 13A to the receptor fiber 13B is then potentially complete by way of the mirror 6. Completion or interruption of the light-path depends on which bistable condition the opaque buckets 8a and 8b are in. The fiberoptic cable 13 provides an important safety feature in that cable 13 completely electrically isolates the patient 1 from the control and alarm devices 14 through 18. The mirror may be replaced by placing small reflective surface RS on the near side of assembly 8 as shown in FIG. 3.

Figure 3A:
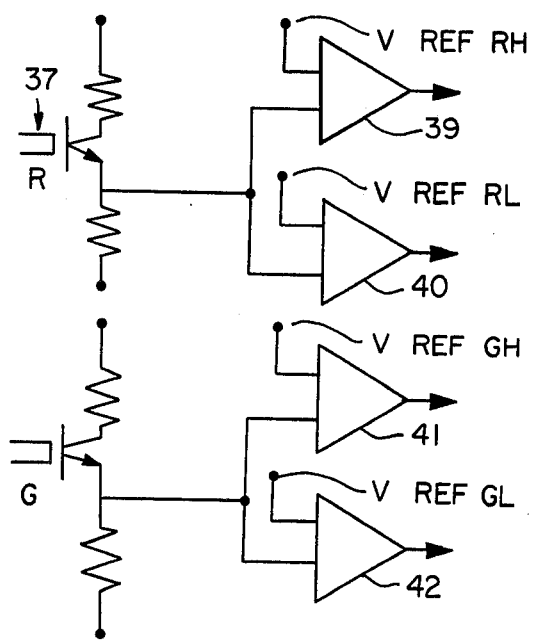
FIG. 3a shows the circuitry employed with the sensors used to detect the presence of blood in the urine.

Similarly shown in FIG. 3 is a second set 31 of fiberoptic channels. This set is made up of three channels or bundles 31A, 31B and 31C, all held by holder 4 at 4b and focussed toward the terminus of catheter 2 in the metering chamber. Bundle 31A directs white light towards mirror 35 (arranged on the wall of holder 4) from light source 36, while bundle 31B is provided with a red filter 33 and bundle 31C is preceded by a green filter 32. This optical circuit 31 serves to note the appearance of hemoglobin in the measuring chamber. Phototransistors 37 and 38 detect the relative signal strength of the reflected signal which passes through drop 24 to detect the presence of hemoglobin. Changes in the amount of red and green light present are detected by comparators 39 through 42 shown in FIG. 3a. The signal representing the intensity of red light is compared against normal upper and lower levels $V_{RefRH}$ and $V_{RefRL}$. When the intensity is outside these limits, i.e. above $V_{RefRH}$ or below $V_{RefRL}$, the signals developed by comparators 39 and 40 indicate an alarm condition. The comparators 41, 42 and the reference levels $V_{RefGH}$ and $V_{RefGL}$ function in a similar fashion with regard to changes in the intensity of green light. If desired, one of the sets of comparators 39, 40 or 41, 42 may be eliminated.

In order to measure the amount of liquid collected, the status of the light path of bundle 13 is sensed by the fiberoptic sensor 14B which may be a phototransistor. A relay within circuit 14 actuates a counter 15 upon a change in the reflected light due to the tilting action of bucket assembly 8. Alternatively, the output of phototransistor 14B may be directly connected to the counter 15 which is preferably of the electromechanical or electronic type. If each bucket 8a, 8b is designed to contain ten cubic centimeters of liquid, for example, a counter can be used with the lowest digit fixed at 0. A resettable timer 16 is coupled to sensor 14B. This timer, which may be a type 555 solid state timer, is initially set so as to have a delay period which slightly exceeds the permissible time for the production of ten cubic centimeters of urine. This permissible time is manually set by adjusting the delay (i.e. R-C) elements of the type 555 timer and depends on the individual patient. If sensor 14B generates a signal within the permissible time, i.e. before timer 16 times out, then timer 16 is reset to 0 elapsed time for the subsequent filling cycle. If sensor 14B fails to generate a signal within the set time interval, the timer 16 times out and actuates alarm 17 which may include an audible and/or lamp alarm. An event or totalizing recorder 18 is an optional part of the system. The counter may be Kessler-Ellis No. E-14-11. The timer 16 may alternatively be Industrial Timer Corp Model GTD operated by a relay coupled to sensor 14B, as is disclosed in my aforesaid patent. Bundle 31 similarly terminates within 14, and is therein provided with two light sensors, suitable circuitry and a relay for alarm closure to generate an alarm when a critical condition is present.

Figures 2A, 2B:
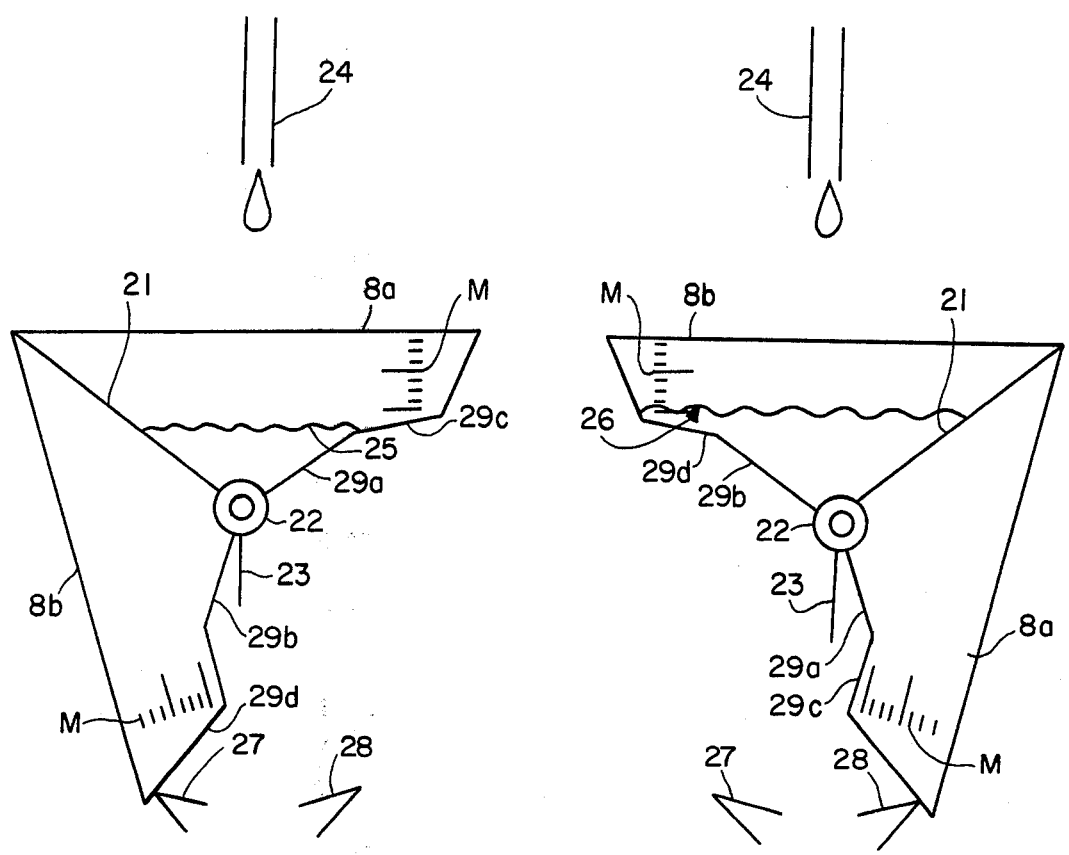
FIG. 2 illustrates the metering device in greater detail.

FIGS. 2A and 2B show the details of the dual chambered bistable metering configuration. The two chambers are identical and symmetrical mirror images of one another, and are separated by a common barrier 21. The configuration is suspended over a pivot point 22 by the support wire 23, which holds pivot support 22 in place. Urine is dispensed from the bottom end of spout 24, and initially fills the triangular-shaped liquid receiving portion formed of surfaces 21 and 29a which portion is immediately above and symmetrically arranged relative to the pivot point 22. The configuration is maintained in the attitude shown in FIG. 2a by the weight and position of the then empty companion chamber 8b. When the liquid level reaches that shown by the wavy line 25 and covering surface 29c, further filling disposes the configuration of the assembly 8 to tilt into the other stable condition shown in FIG. 2B due to the unsymmetrical relation between surface 21 and surface 29c which shifts the center of gravity of the liquid away from imaginary line 12 (see FIG. 1). The level that will cause the flipping is indicated by wavy line 26. Members 27 and 28 designate stationary mounted stops for the two bistable conditions and limit the pivoting movement. The tilting operation alternates as the collection operation progresses. Liquid dispensed may be collected in container 9.

The walls of the two chambers are provided with horizontal (when in fill position) level marks M. These marks facilitate visual interpretation of urine levels prior to the filled bucket tilting, i.e., the non-automatic reading of a fluid quantity less than the unit amount needed to tilt the assembly.

A latitude of modification, change and substitution is intended in the foregoing disclosure, and in some instances, some features of the invention will be employed without a corresponding use of other features. For example, the receptacles 8a and 8b may be different in size to accommodate different amounts of liquid. Accordingly, it is appropriate that the appended claims be construed broadly and in a manner consistent with the spirit and scope of the invention herein.

What is claimed is:

1. Apparatus for measuring a liquid comprising:
    a conduit having an inlet for receiving the liquid and having an outlet;
    a pivotally mounted bistable receptacle assembly having first and second open ended liquid-receiving recesses, spaced from one another;
    said bistable receptacle assembly having first and second stable positions wherein said first and second recesses are respectively positioned beneath the outlet of said conduit;
    the recess positioned beneath said outlet being retained in the liquid receiving position by the recess displaced from said outlet until a predetermined quantity of liquid is collected therein and having a configuration which moves the receptacle to position the recess displaced from said outlet to the position beneath said outlet and displace the recess presently containing liquid away from said outlet when the quantity of liquid surpasses said predetermined level, whereby the last-mentioned recess dispenses its contents, each of said recesses having a first portion for initially receiving liquid which first portion is shaped to locate the center of gravity of the liquid filling said first portion to be coincident with an imaginary vertical line passing through the pivotal mounting of said bistable receptacle assembly, so that the liquid filling said first portion is prevented from tilting the bistable receptacle as the first portion of the recess is being filled and regardless of the weight of its contents;
    each of said recesses further having a second portion for receiving liquid once the first portion thereof is filled, said second portion being shaped to displace the center of gravity of the liquid away from said imaginary line as said second portion is being filled to permit the bistable receptacle to tilt and thereby move the recess being filled away from said outlet.

2. The apparatus of claim 1 wherein said first and second recesses are symmetrically disposed on opposite sides of a common barrier arranged therebetween.

3. The apparatus of claim 1 further comprising a disposable collector positioned beneath said bistable receptacle assembly for receiving liquid dispensed from said assembly.

4. The apparatus of claim 3 wherein said receptacle is provided with indicia associated with each of said recesses to facilitate a determination of the amount of liquid collected therein.

5. The apparatus of claim 3 further comprising a holder for releasably supporting said collector beneath said bistable receptacle assembly.

6. The apparatus of claim 1 further comprising sensor means responsive to each movement of said liquid receiving means away from a stable position for generating a signal; and
    means for counting said signals.

7. The apparatus of claim 6 further comprising recording means responsive to said sensor means for recording said signals.

8. The apparatus of claim 1 further comprising sensor means responsive to each movement of said bistable receptacle away from a stable position for generating a signal;
    resettable timer means including timer means responsive to said sensor means and being reset upon the occurrence of each signal; and
    alarm means responsive to said timer means for generating an alarm in the event that the timer means times out before being reset.

* * * * *

UNITED STATES PATENT AND TRADEMARK OFFICE
CERTIFICATE OF CORRECTION

PATENT NO. : 4,417,585
DATED : November 29, 1983
INVENTOR(S) : ULRICH A. FRANK

It is certified that error appears in the above—identified patent and that said Letters Patent is hereby corrected as shown below:

Column 2, line 41, "The" should read --This--.

Column 3, line 25, "tiltable" should be --tiltably--.

Signed and Sealed this

Seventh Day of February 1984

[SEAL]

Attest:

GERALD J. MOSSINGHOFF

Attesting Officer

Commissioner of Patents and Trademarks